(12) United States Patent
Bogdanovic et al.

(10) Patent No.: US 6,388,142 B1
(45) Date of Patent: May 14, 2002

(54) METHOD FOR PRODUCING ALDEHYDES BY HYDROFORMYLATION IN THE PRESENCE OF CROWN ETHER

(75) Inventors: Sandra Bogdanovic, Frankfurt; Klaus Kuhlein, Kelkheim, both of (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 09/509,143

(22) PCT Filed: Sep. 8, 1998

(86) PCT No.: PCT/EP98/05683

§ 371 Date: May 16, 2000

§ 102(e) Date: May 16, 2000

(87) PCT Pub. No.: WO99/15488

PCT Pub. Date: Apr. 1, 1999

(30) Foreign Application Priority Data

Sep. 25, 1997 (DE) .......................................... 197 42 305

(51) Int. Cl.[7] .............................................. C07C 45/50
(52) U.S. Cl. ....................................... 568/454; 568/451
(58) Field of Search ................................ 568/451, 454

(56) References Cited

U.S. PATENT DOCUMENTS

| 4,320,064 A | * | 3/1982 | Vidal ..................... 260/429 R |
| 4,399,312 A |   | 8/1983 | Russel et al. |
| 4,731,486 A |   | 3/1988 | Abatjoglou et al. |
| 5,091,350 A | * | 2/1992 | Cornils et al. ................. 502/24 |

FOREIGN PATENT DOCUMENTS

| EP | 0302375 | 2/1989 |
| EP | 0491239 | 6/1992 |
| EP | 0571819 | 12/1993 |

* cited by examiner

*Primary Examiner*—Sreeni Padmanabhan
(74) *Attorney, Agent, or Firm*—Bierman, Muserlian and Lucas

(57) ABSTRACT

The invention relates to a method for producing aldehydes by reacting one olefine containing 3 to 12 carbon atoms with hydrogen and carbon monoxide in the presence of one rhodium catalyst. The invention is characterized in that (a) the rhodium catalyst is present in an aqueous phase, whereby the aqueous phase contains i) rhodium in an elemental or bonded form, ii) one trisulfonated triaryl phosphine, and iii) one crown etherl (b) the olefine is present in the reaction conditions in a liquid organic phase which cannot be mixed with the aqueous phase.

20 Claims, No Drawings

METHOD FOR PRODUCING ALDEHYDES BY HYDROFORMYLATION IN THE PRESENCE OF CROWN ETHER

This application is a 371 of PCT/EP98/05683 filed Sep. 8, 1998.

The present invention relates to a process for the hydroformylation of olefinically unsaturated compounds having 3 to 12 carbon atoms with hydrogen and carbon monoxide at increased pressure.

In the hydroformylation of olefins with carbon monoxide and hydrogen aldehydes and alcohols are produced with the aldehydes and alcohols having one carbon atom more than the starting olefin. The catalyst is herein conventionally used in homogeneous phase with the olefin. The reaction is preferably catalyzed by hydridometal carbonyles of the metals of group VIII of the periodic table of elements. Apart from cobalt, which is used extensively as a catalyst metal in technical applications, rhodium has acquired increasing significance preferably for the hydroformylation of lower olefins. In contrast to cobalt, rhodium permits carrying out the reaction at low pressure, moreover, when using terminal olefins preferably straight-chain n-aldehydes are formed and only secondary iso-aldehydes. Furthermore, the hydrogenation of the olefinic compounds to form saturated hydrocarbons in the presence of rhodium catalysts is also markedly lower than is the case when using cobalt catalysts.

In methods introduced in technology the rhodium catalyst is used in the form of modified hydridorhodium carbonyles, which additionally and, if appropriate, comprise ligands in excess. Especially useful have been found to be ligands of tertiary phosphines or phosphites. Their application permits lowering the reaction pressure to values below 30 MPa.

For example, DE 27 43 630 relates to the production of alkane polyols (glycols) from synthesis gas using a crown ether comprising at least 4 oxygen atoms as solvent. This crown ether serves for separating ions from the homogeneous liquid phase without the simultaneous complex formation of the rhodium-containing catalyst. The reaction temperatures in all examples are above 220° C.

In U.S. Pat. No. 4,320,064 is described the reaction of carbon monoxide with hydrogen to form polyols using rhodium carbonyl clusters in a homogeneous liquid phase. As the catalyst a cesium salt of $[Rh_{22}(CO)_{35}H_x]^{n-}$ complexed by 18-crown-6 is used. Here also the crown ether serves for the complexing of the cationic component of the rhodium carbonyl cluster. The temperatures specified in the examples are between 250 and 270° C.

However, in these methods the separation of the reaction products and the recovery of the catalysts homogeneously dissolved in the reaction product presents problems. In general, for this purpose, the conversion product is distilled out of the reaction mixture. Due to the thermal sensitivity of the formed aldehydes and alcohols, this approach can only be followed in practice in the hydroformylation of short-chain olefins with 3 to 5 carbon atoms.

In the hydroformylation of olefins with more than 6 carbon atoms, products with high boiling point are formed which cannot be separated by distillation from the homogeneously dissolved rhodium complex catalyst. Through the formation of heavy oil, the thermal loading of the distillation material leads to considerable losses of valuable products and of catalysts through the decomposition of the rhodium complex compounds.

The problem of thermal decomposition is avoided if a two-phase catalysis is used. Herein two liquid phases not miscible with one another are present of which the one organic phase contains the olefin and the other, most often polar phase, contains the catalyst. Prerequisite for the application of this process is the solubility of the catalyst in the polar phase. On an industrial scale as the polar phase is used an aqueous phase and as the catalyst a rhodium complex compound. The solubility of the catalyst in the aqueous phase is herein attained by using sulfonated triaryl phosphines as complex component. After completing the hydroformylation reaction, the separation of the catalyst from the reaction product in this process variant takes place simply by separation of the aqueous and organic phase, i.e. without distillation and thus without additional thermal process steps. Such a process is described for example in DE 26 27 354. A special characteristic of this mode of operation is that from terminal olefins with high selectivity are formed n-aldehydes and only to a minor degree iso-aldehydes (i.e. aldehydes branched in the α position to the aldehyde group). In addition to sulfonated triaryl phosphines, carboxylated triaryl phosphines are also used as complex components water-soluble rhodium complex compounds.

The use of a water-soluble catalyst has also been found to be useful in the hydroformylation of lower olefins, in particular propene and butene. However, if higher olefins such as pentene or hexene are used, the conversion rate is already markedly reduced. The economy of the conversion on an industrial scale is frequently no longer given to the desired extent when using olefins with more than four carbon atoms.

In order to increase in the hydroformylation of olefins with more than 5 carbon atoms by means of water-soluble catalysts the conversion and/or the selectivity of the reaction to n-aldehydes, special amphiphilic reagents or solubilizers have also been used.

The addition of these substances leads to the fact that the transport of matter between the discrete phases and thus the miscibility of the aqueous catalyst phases and organic phase are promoted.

DE 34 12 334, for example, relates to the hydroformylation of olefins using quaternary ammonium salts. As is evident in Table 4, the hydroformylation of hexene by means of rhodium and trisodium tris(m-sulfophenyl)phosphine without the addition of a solubilizer leads to a conversion of 36% (Example 10), while the addition of polyols as solubilizer (Example 11: 5% polyglycol 200; Example 14: 2.5% triethylene glycol) only brings about a conversion of 43.5% or 43%, respectively. A very high conversion, 86%, in contrast, is attained through the addition of 2.5% trimethyl hexadecyl ammonium bromide as solubilizer. This publication shows that only the addition of quaternary ammonium salts causes a considerable increase in the conversion. In contrast, neither the addition of tri- or polyglycols, not an increase of the quantity of these substances by the twofold (from 2.5 to 5%) causes a significant increase of the conversion.

In DE 31 35 127 A1 the hydroformylation of olefins is described using amphiphilic reagents in the presence of a rhodium catalyst complexed by a phosphine ligand. Table 7 shows that the hydroformylation of 1-dodecene by means of rhodium and monosulfonated triphenyl phosphine (3-$Ph_2PC_6H_4SO_3Na$) without the addition of an amphiphilic reagent leads to a conversion of 56% (Example 77), while the addition of 18-crown-6 leads to a decrease of the conversion to 40% (Example 57). In this case also high yields are only attained by using quaternary ammonium salts (Example 68: 85% with CTAB).

A substantial disadvantage in using quaternary ammonium salts as amphiphilic reagents lies, however, in their poor biological degradability. For example, the presence of quaternary ammonium salts in the waste water leads to considerable difficulties in waste water treatment.

A further disadvantage in using quaternary ammonium salts as solubilizers lies therein that the increase of the miscibility of the aqueous catalyst phase and the organic phase achieved with these compounds is accompanied by increased solubility of the organic phase in the aqueous phase and of the aqueous phase in organic phase. In this way, to an increasing degree amphiphilic reagent and solubilizer as well as also rhodium and water-soluble phosphines can be present in the organic phase and, after phase separation, can be discharged with the organic phase. It is understood that the discharge of these substances via the organic phase is undesirable since new substances must again be added to the same extent to the aqueous phase to the same extent, which, in particular in view of rhodium, entails considerable increased financial expenditures.

Furthermore, with a higher addition of amphiphilic reagents or solubilizer—i.e. with increased miscibility of the aqueous catalyst phase and the organic phase—the separation into components necessary for the phase separation no longer takes place or takes place to an insufficient extent due to the formation of emulsions or solutions. This is in particular the case with such amphiphilic reagents which can also be used as tensides or foaming agents.

This is of disadvantage since good separation into components is an indispensable prerequisite for the required separation, completing the hydroformylation, of organic and aqueous phase.

The task of the invention comprises providing a process for the production of aldehydes through the hydroformylation of olefins with 3 to 12 carbon atoms, which makes possible greater conversions in comparison to prior art and which avoids the disadvantages of prior art.

This task is solved through a process for the production of aldehydes through the conversion of an olefin with 3 to 12 carbon atoms with hydrogen and carbon monoxide in the presence of a rhodium catalyst, characterized in that
(a) the rhodium catalyst is present in an aqueous phase with the aqueous phase comprising
  i) rhodium in elementary or bound form;
  ii) a trisulfonated triaryl phosphine, and
  iii) a crown ether, and
b) the olefin under the reaction conditions is present in a liquid organic phase which is not miscible with the aqueous phase.

The process according to the invention is in particular distinguished thereby that in comparison to prior art, higher conversions with high selectivity are attained and that no significant rise of rhodium or ligand in the organic phase and thus no increased discharge of the catalyst via the organic phase is observed.

Furthermore, the capacity for being separated of the organic phase and the aqueous catalyst phase is so high that a rapid separation of organic phase and aqueous phase is ensured. When applying this process neither emulsions difficult of separation nor nonseparatable homogeneous solutions are formed.

The crown ethers to be used according to the invention are described for example in "Ullmann's Encyclopedia of Industrial Chemistry" Weinheim (1987), Fifth Edition, Volume A8, pp. 91–97.

The trisulfonated triaryl phosphine is, according to a preferred embodiment a trisulfonated triaryl phosphine having the formula (I)

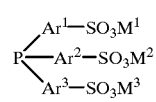

(I)

in which $Ar^1$, $Ar^2$ and $Ar^3$ independently of one another represent a phenyl, naphthyl, biphenyl, phenylnaphthyl or binaphthyl group;

$M^1$, $M^2$ and $M^3$ independently of one another represent an alkali metal ion or an ammonium ion.

But it is also possible that $M^1$, $M^2$ and $M^3$ represent different higher cations such as, for example, alkaline earth or zinc ions, with the charge equalization determining decisively the number of these cations.

This trisulfonated triaryl phosphine having the formula (I) is especially preferably trisodium tris(m-sulfophenyl) phosphine having the formula

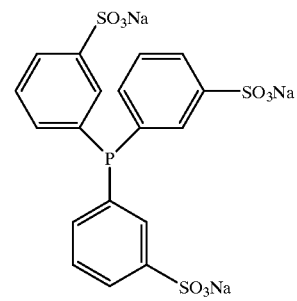

Due to its production by sulfonation of triphenyl phosphine, this trisodium salt contains fractions of mono- and disulfonated compounds and small fractions of the corresponding phosphine oxides.

The trisulfonated triaryl phosphine can also be a sulfonated triaryl phosphine with two phosphorus atoms, which comprises, for example, a group —$(CH_2)_x$—Ar—Ar—$(CH_2)_x$— in which x represents an integer between 1 and 4, in particular 1 to 2, preferably 1, Ar—Ar is biphenyl or binaphthyl, the group —$(CH_2)_x$ with one bond is in the ortho position with respect to the aryl-aryl bond Ar—Ar connecting the two aryl groups, and with the other bond is bound to one phosphorus atom which has two further, identical or different aryl groups, in particular phenyl groups.

Examples of such trisulfonated triaryl phosphines having two phosphorus atoms are compounds having the formula (II)

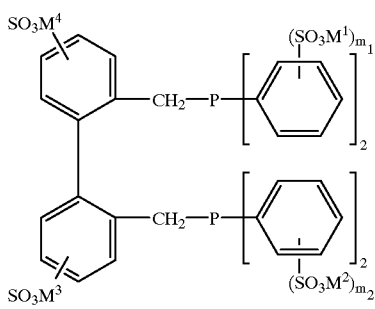

(II)

in which
m$^1$ and m$^2$ can have the value 0 or 1, with the sum of m$^1$ and m$^2$ being at least 1, and M$^1$, M$^2$, M$^3$ and M$^4$ independently of one another represent each an alkali metal ion or an ammonium ion. But is also possible that M$^1$, M$^2$, M$^3$ and M$^4$ represent different, higher cations such as for example alkaline earth or zinc cations with the charge equalization decisively determining the number of these cations.

The organic trisulfonated triaryl phosphine can also be a compound having the formula (III)

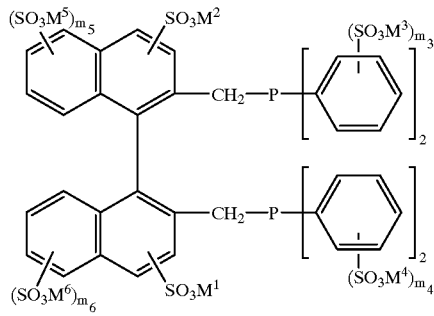

(III)

in which
m$_3$, m$_4$, m$_5$ and m$_6$ can have the value 0 or 1, with the sum of m$_3$, m$_4$, m$_5$ and m$_6$ being at least 2, and M$^1$, M$^2$, M$^3$, M$^4$, M$^5$ and M$^6$ independently of one another represent each an alkali metal ion or an ammonium ion.

In this case it is also possible that M$^1$, M$^2$, M$^3$, M$^4$, M$^5$ and M$^6$ represent different, higher cations, such as for example alkaline earth or zinc cations, with the charge equalization decisively determining the number of these cations.

Such triaryl phosphines containing two phosphorus atoms of formula (II) and (III) comprise in particular four to eight —SO$_3$M groups. The —SO$_3$M are customarily located at the aryl groups of the group —(CH$_2$)$_x$—Ar—Ar—(CH$_2$)$_x$— and at the two further aryl groups bound to the phosphorus.

Instead of sulfonated triaryl phosphines, other triaryl phosphines can alternatively be used as ligands, in which the SO$_3$M group is substituted by other groups which bring about the water solubility of the triaryl phosphine, such as for example PO$_3$M$_2$ groups.

According to an especially preferred embodiment, the crown ether is selected from the group 12-crown-4, 15-crown-5, 18-crown-6 and hydroxy methyl 18-crown-6.

The olefin can be selected from aliphatic, cycloaliphatic and araliphatic olefins, in particular from aliphatic and cycloaliphatic α-olefins.

The olefinic compound can comprise one or several carbon-carbon double bonds. The carbon-carbon double bond can be terminal or nonterminal. Preferred are olefinic compounds with terminal carbon-carbon double bonds. Examples of α-olefinic compounds (with terminal carbon-carbon double bond) are 1-alkenes, alkylalkenoates, alkylene alkanoates, alkenyl alkyl ethers and alkenols. Without claiming completeness, as α-olefinic compounds are cited propene, 1-butene, 1-pentene, 1-hexene, 1-heptene, 1-octene, 1-nonene, 1-decene, 1-undecene and 1-dodecene.

Especially preferred are olefins which contain maximally 10, preferably maximally 8 carbon atoms.

In view of the industrial use of this process, the olefin is in particular selected from the group propene, 1-butene, 1-pentene and 1-hexene.

In view of the process according to the invention it was found to be optimal that the aqueous phase comprises 20 to 500 ppm, preferably 30 to 150 ppm, in particular 40 to 100 ppm, of rhodium. The ratio of rhodium to ligand can herein be between 1:10 and 1:1000, preferably between 1:50 and 1:200.

The aqueous phase comprising the catalyst can be produced in a comparatively simple manner, by dissolving in water a water-soluble rhodium salt, the trisulfonated triaryl phosphines and the compound having the formula (I). Without claiming completeness, suitable rhodium salts are: rhodium(III) sulfate, rhodium(III) nitrate, rhodium(III) carboxylates such as rhodium(III) acetate, rhodium propionate, rhodium butyrate and rhodium-2-ethylhexanoate. The aqueous phase can be used directly in the hydroformylation or be previously subjected to a performulation of the catalyst under reaction conditions in order to use it subsequently in the performulated form.

The aqueous phase can preferably comprise $2\times10^{-6}$ to $5\times10^{-2}$ mol of rhodium per mol of olefinic compound.

During the reaction the pressure is in general between 20 and 150 bars, preferably between 30 and 80 bars. The ratio of carbon monoxide and hydrogen can vary within wide limits. Optimal is a ratio of carbon monoxide to hydrogen of 10:1 to 1:30, in particular of 5:1 to 1:8, preferably of 1:2 to 2:1. Especially preferred is the addition under pressure of synthesis gas at a ratio of carbon monoxide to hydrogen of 1:1.

During the reaction the temperature is customarily between 20 and 170° C., preferably between 100 and 140° C.

As the reaction vessels are used pressure reactors with magnetic or mechanical agitating or mixing devices. During the conversion a thorough mixing of the phases present, i.e. of polar phase, carbon monoxide/hydrogen and, if appropriate, organic phase must be ensured. This can be brought about in particular by intensive agitation and/or transferring by pumping of organic and aqueous phase. Continuous guidance of the experiment is also possible.

At the end of the reaction the pressure reactor is cooled, freed of carbon monoxide and hydrogen by pressure reduction and the reaction mixture is removed. After the mixing device is switched off, the phases separate by themselves within seconds. The organic phase can be processed by distillation and subsequently, if required, be analyzed by gas chromatography.

The following examples serve to explain the invention.

EXAMPLE 1 (COMPARISON EXAMPLE)

a): Production of the catalyst phase and preformulation 60 mg (0.23 mmol) rhodium(III) acetate are dissolved in 39 ml of a 0.6 M aqueous solution of the trisodium salt of TPPTS (tris-(metasulfonato)triphenyl phosphine) corresponding to a molar ratio of rhodium to ligand of 1:100 and 21 ml of degassified distilled water and placed into a 200 ml steel autoclave under nitrogen. The catalyst solution produced in this way is heated at 25 bars of synthesis gas pressure ($CO/H_2=1/1$) over 3 hours to 125° C. in which the active catalyst complex is formed and the solution assumes a strong yellow color.

b): Hydroformylation

To the preformulated catalyst solution from 1.a) are added at a reaction pressure of 30 bars and at 125° C. 26.3 ml 1-pentene (240 mmol) via a preceding 200 ml steel autoclave with slight excess pressure. The ratio of olefin to rhodium is 1030:1. The hydroformylation reaction is initiated by switching on the magnetic stirrer. During a reaction time of 3 hours the temperature is maintained at 125° C. and the reaction pressure is kept constant within a pressure band of ±3 bars by manually adding synthesis gas. After a period of 3 hours, agitator and heating are switched off, the autoclave is cooled to 40 to 50° C. and the upper product phase is separated from the catalyst phase by means of phase separation in a separating funnel. Product phase and catalyst phase are weighed. The composition of the product phase is determined by means of gas chromatography and NMR-$^1$H spectroscopy and from the composition the yield of hydroformylation products and the ratio of n to iso heptanal is determined.

The yield of hydroformylation products is 49.4%, the n/iso ratio is 96:4.

EXAMPLE 2 a): Production of the catalyst phase and performulation 30 mg (0.166 mmol) rhodium(III) acetate are dissolved in 19.5 ml of a 0.6 M aqueous solution of the trisodium salt of TPPTS (tris-(metasulfonato) triphenyl phosphine) and mixed with 2.88 g of the crown-ether 18-crown-6. This catalyst phase is placed under nitrogen into a 200 ml steel autoclave and heated at 25 bars synthesis gas pressure ($CO/H_2=1/1$) over 3 hours to 125° C.

b): Hydroformylation

To the performulated catalyst solution from 2.a) are added 13.2 ml 1-pentene (120 mmol). The hydroformylation is carried out analogously to Example 1.a) at 125° C. and at 50 bars synthesis gas. The composition of the product phase is determined by means of gas chromatography and NMR-$^1$H spectroscopy and, based on the composition, the degree of conversion and the selectivity are determined. The yield of hydroformylation product is 86.7%, the n/iso ratio is 94:6.

EXAMPLES 3 TO 28

The comparison examples 14 to 20 are carried out analogously to Example 1 to 125° C. and 50 bars. The examples 3 to 13, 15 to 19 and 21 to 24 according to the invention are carried out analogously to Example 2. In all examples according to the invention a 0.6 M aqueous solution of the trisodium salt of TPPTS (Tris-(metasulfonato) triphenyl phosphine) is used corresponding to a molar ratio of rhodium to ligand of 1:100. The specifications with respect to quantities of rhodium(III) acetate and TPPTS solution, the ratio of olefin to rhodium as well as the educts and reaction results are compiled in Table 1.

In Table 1 the following terms are used:

"Olefin" denotes the olefin used,

"Rh cat" indicates the quantity in mmol of the rhodium catalyst,

"Ol/rh ratio" indicates the molar ratio of olefin to rhodium,

"TPPTS" represents the quantity in ml of 0.6 M aqueous solution of tris-(metasulfonato) triphenyl phosphine, "Crown" represents the crown ether used and its quantity, herein 12-C-4 represents 12-crown-4, 15-C-5 represents 15-crown-5, 18-C-6 18-crown-6 and 18-C-6-OH hydroxymethyl-18-crown-6 (($CH_2$—$CH_2$—$O)_5$—$CH_2$—$CH(CH_2OH)O$), "Wt. % crown" indicates the fraction of crown ether used, relative to the catalyst phase, "$H_2O$" indicates the quantity of water in ml added to the aqueous phase, "t" represents the reaction time in minutes, "n:iso" indicates the ratio of n-aldehydes to iso-aldehydes; "n.d." (not determinable) indicates herein that the ratio cannot be determined due to the low conversion.

TABLE 1

| Example | Olefin [mmol] | RH Cat [mmol] | Ol/Rh Ratio | TPPTS [ml] | Crown [g] | Wt. % Crown | $H_2O$ [ml] | t [min] | Conversion [%] | n:iso |
|---|---|---|---|---|---|---|---|---|---|---|
| 1* | 240 (1-pentene) | 0.233 | 1030 | 39 | — | — | 21 | 180 | 49.4 | 96:4 |
| 2 | 120 (1-pentene) | 0.166 | 1030 | 19.5 | 2.88 (18-C-6) | 11.38 | 0 | 200 | 86.7 | 94:6 |
| 3 | 120 (1-pentene) | 0.166 | 1030 | 19.5 | 5.75 (18-C-6) | 20.41 | 0 | 120 | 90.6 | 91:9 |
| 4 | 120 (1-pentene) | 0.166 | 1030 | 19.5 | 6.64 (18-C-6) | 27.81 | 0 | 120 | 92.6 | 88:12 |
| 5 | 120 (1-pentene) | 0.166 | 1030 | 19.5 | 2.88 (18-C-6) | 8.65 | 8 | 190 | 89.0 | 94:6 |
| 6 | 120 (1-pentene) | 0.166 | 1030 | 19.5 | 5.75 (18-C-6) | 17.07 | 5.5 | 120 | 89.1 | 92:8 |
| 7 | 120 (1-pentene) | 0.166 | 1030 | 19.5 | 8.64 (18-C-6) | 25.36 | 3 | 90 | 84.5 | 92:8 |
| 8 | 120 (1-pentene) | 0.166 | 1030 | 19.5 | 2.88 (12-C-4) | 11.38 | 0 | 180 | 85.0 | 95:5 |
| 9 | 120 (1-pentene) | 0.166 | 1030 | 19.5 | 2.88 (15-C-5) | 11.38 | 0 | 180 | 81.0 | 95:5 |
| 10 | 120 (1-pentene) | 0.058 | 2060 | 9.75 | 6.04 (18-C-6) | 35.01 | 0 | 105 | 85.1 | 85:15 |
| 11 | 120 (1-pentene) | 0.166 | 1030 | 19.5 | 2.88 (12-C-4) | 8.65 | 8 | 180 | 81.3 | 95:5 |

TABLE 1-continued

| Example | Olefin [mmol] | RH Cat [mmol] | Ol/Rh Ratio | TPPTS [ml] | Crown [g] | Wt. % Crown | $H_2O$ [ml] | t [min] | Conversion [%] | n:iso |
|---|---|---|---|---|---|---|---|---|---|---|
| 12 | 120 (1-pentene) | 0.166 | 1030 | 19.5 | 2.88 (15-C-5) | 8.65 | 8 | 180 | 85.9 | 94:6 |
| 13 | 60 (1-pentene) | 0.058 | 1030 | 9.75 | 1.00 (18-C-6-OH) | 6.17 | 4 | 180 | 83.6 | 95:5 |
| 14* | 240 (1-hexene) | 0.233 | 1030 | 39 | — | — | 21 | 180 | 34.7 | 96:4 |
| 15 | 60 (1-hexene) | 0.058 | 1030 | 9.75 | 2.94 (12-C-4) | 20.77 | 0 | 180 | 65.5 | 93:7 |
| 16 | 60 (1-hexene) | 0.058 | 1030 | 9.75 | 2.94 (18-C-6) | 20.77 | 0 | 140 | 72.3 | 91:9 |
| 17 | 60 (1-hexene) | 0.058 | 1030 | 9.75 | 5.75 (18-C-6) | 25.60 | 5.5 | 180 | 90.2 | 86:14 |
| 18 | 60 (1-hexene) | 0.058 | 1030 | 9.75 | 5.75 (12-C-4) | 25.60 | 5.5 | 130 | 76.9 | 89:11 |
| 19 | 120 (1-hexene) | 0.058 | 2060 | 9.75 | 5.75 (18-C-6) | 25.60 | 5.5 | 180 | 80.5 | 87:13 |
| 20* | 240 (1-octene) | 0.233 | 1030 | 39 | — | — | 0 | 180 | 7.6 | 95:5 |
| 21 | 60 (1-octene) | 0.058 | 1030 | 9.75 | 6.04 (12-C-4) | 35.01 | 0 | 180 | 57.0 | 86:14 |
| 22 | 60 (1-octene) | 0.058 | 1030 | 9.75 | 6.04 (18-C-6) | 35.01 | 0 | 180 | 61.4 | 82:18 |
| 23 | 60 (1-octene) | 0.058 | 1030 | 9.75 | 3.02 (18-C-6) | 21.22 | 0 | 180 | 39.0 | 99:1 |
| 24 | 60 (1-octene) | 0.058 | 1030 | 9.75 | 4.53 (18-C-6) | 28.78 | 8 | 180 | 71.2 | 82:18 |

* = Comparison Example

What is claimed is:

1. In a process for the production of aldehydes by hydroformylation of olefins of 3 to 12 carbon atoms with hydrogen and carbon monoxide in the presence of a rhodium catalyst, the improvement comprising a) the rhodium catalyst is present in an aqueous phase comprising i) rhodium in elementary or bound form, ii) a trisulfonated triarylphosphine having 1 to 2 phosphorus atoms and iii) a crown ether and b) the olefin under the reaction conditions is present in a liquid organic phase not miscible with the aqueous phase.

2. The process as claimed in claim 1 wherein the crown ether is selected from the group consisting of 12-crown-4, 15-crown-5, 18-crown-6 and hydroxymethyl-18-crown-6.

3. The process of claim 1 wherein the olefin is selected from the group consisting of aliphatic, cycloaliphatic and araliphatic olefins.

4. The process of claim 1 wherein the olefin is selected from the group consisting of propene, 1-butene, 1-pentene, 1-hexene, 1-heptene, 1-octene, 1-nonene, 1-decene, 1-undecene and 1-dodecene.

5. The process of claim 1 wherein the olefin has maximally 10 carbon atoms.

6. The process of claim 1 wherein the ratio of rhodium to ligand is between 1:10 and 1:1000.

7. The process of claim 1 wherein the aqueous phase contains 20 to 500 ppm of rhodium.

8. The process of claim 1 wherein the aqueous phase contains $2\times10^{-6}$ to $5\times10^{-2}$ mol of rhodium per mol of olefinic compound.

9. The process of claim 1 wherein the pressure during the reaction is between 20 and 150 bars.

10. The process of claim 1 wherein the temperature during the reaction is between 20 and 170° C.

11. The process of claim 3 wherein the olefin is an aliphatic α-olefin or a cycloaliphatic olefin.

12. The process of claim 5 wherein the olefin has at most 8 carbon atoms.

13. The process of claim 6 wherein the rhodium to ligand ratio is 1:50 to 1:200.

14. The process of claim 7 wherein the aqueous phase contains 40 to 100 ppm of rhodium.

15. The process of claim 9 wherein the pressure is 30 to 80 bars.

16. The process of claim 10 wherein the temperature is 100 to 140° C.

17. The process of claim 1 wherein the trisulfonated triarylphosphine has the formula

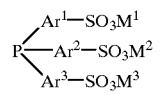

I wherein $Ar^1$, $Ar^2$ and $Ar^3$ are individually selected from the group consisting of phenyl, naphthyl, biphenyl, phenylnaphthyl and binaphthyl and $M^1$, $M^2$ and $M^3$ are individually alkali metal ion or ammonium ion.

18. The process of claim 1 wherein the trisulfonated triarylphosphine is trisodium tris(m-sulfophenyl)-phosphine.

19. The process of claim 1 wherein the trisulfonated triarylphosphine has the formula

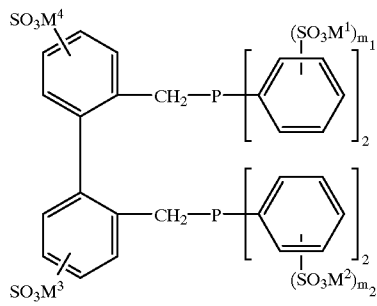

II

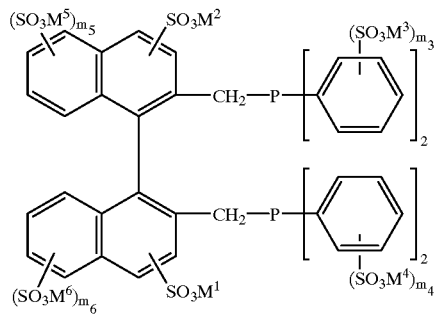

III

20. The process of claim 1 wherein the trisulfonated triarylphosphine has the formula where $m^1$ and $m^2$ are 0 or 1 and $m^1+m^2$ is at least 1 and $M^1$, $M^2$, $M^3$ and $M^4$ are individually an alkali metal ion or ammonium ion.

wherein $m^1$, $m^2$, $m^3$ and $m^4$ are individually 0 or 1 and $m^1+m^2+m^3+m^4$ is at least 2 and $M^1$, $M^2$, $M^3$, $M^4$, $M^5$ and $M^6$ are individually alkali metal ion or ammonium ion.

* * * * *